United States Patent [19]
Zeimer et al.

[11] Patent Number: 4,891,043
[45] Date of Patent: Jan. 2, 1990

[54] SYSTEM FOR SELECTIVE RELEASE OF LIPOSOME ENCAPSULATED MATERIAL VIA LASER RADIATION

[75] Inventors: Ran C. Zeimer, Chicago; Bahram Khoobehi, River Forest; Gholam A. Peyman, Chicago, all of Ill.

[73] Assignee: Board of Trustees of the University of Illinois, Chicago, Ill.

[21] Appl. No.: 55,047

[22] Filed: May 28, 1987

[51] Int. Cl.$^4$ ............................................. A61M 1/30
[52] U.S. Cl. ........................................... 604/20; 606/2
[58] Field of Search ............... 128/1 R, 303.1, 898; 540/145; 604/20, 21

[56] References Cited

U.S. PATENT DOCUMENTS

| | | | |
|---|---|---|---|
| Re. 32,066 | 1/1986 | Leveen | 128/804 |
| 4,078,052 | 3/1978 | Papahadjopoulos | 424/36 |
| 4,241,046 | 12/1980 | Papahadjopoulos et al. | 424/19 |
| 4,310,506 | 1/1982 | Baldeschwieler et al. | 424/1 |
| 4,350,676 | 9/1982 | Laties et al. | 424/7 |
| 4,409,979 | 10/1983 | Roussel et al. | 128/303.1 |
| 4,495,949 | 1/1985 | Stoller | 128/303.1 |
| 4,499,897 | 2/1985 | Roussel | 128/303.1 |
| 4,515,736 | 5/1985 | Deamer | 264/4.3 |
| 4,520,816 | 6/1985 | Schacher et al. | 128/303.1 |
| 4,522,803 | 6/1985 | Lenk et al. | 424/1.1 |
| 4,610,868 | 9/1986 | Fountain et al. | 424/1.1 |
| 4,649,151 | 3/1987 | Dougherty et al. | 540/145 |

OTHER PUBLICATIONS

Yatvin et al., "Design of Liposomes for Enhanced Local Release of Drugs by Hyperthermia," Science, vol. 202, pp. 1290-1292, Dec. 22, 1978.

Weinstein et al., "Lipsomes and Local Hyperthermia: Selective Delivery of Methotrexate to Heated Tumors," Science, vol. 204, pp. 188-191, Apr. 13, 1979.

Weinstein et al., "Treatment of Solid L1210 Murine Tumors with Local Hyperthermia and Temperature—Sensitive Liposomes Containing Methotrexate," Cancer Research, vol. 40, pp. 1388-1394, May 1980.

Weinstein et al., "Phase Transition Release, A New Approach to the Interaction of Proteins with Lipid Vesicles, Application to Lipoproteins," Biochimica et Biophysica Acta, vol. 647, pp. 270-284, 1981.

*Primary Examiner*—C. Fred Rosenbaum
*Assistant Examiner*—Kathleen A. Daley
*Attorney, Agent, or Firm*—Roylance, Abrams, Berdo & Goodman

[57] ABSTRACT

A system for selectively releasing materials, such as drugs or dyes, at a specific site in the body of an animal. The system uses laser radiation to rupture laser light-absorbing and heat-sensitive lipid vesicles containing the drugs or dyes, thereby releasing these materials at the specific site irradiated by the laser. By using this system, the location and concentration of the materials are controlled as well as the duration of the materials' release and the release can be triggered repetitively. The laser beam used is visible or its location can be made visible to the naked eye so that the location and size of the beam's contact with the irradiated tissue can be observed and adjusted.

11 Claims, 2 Drawing Sheets

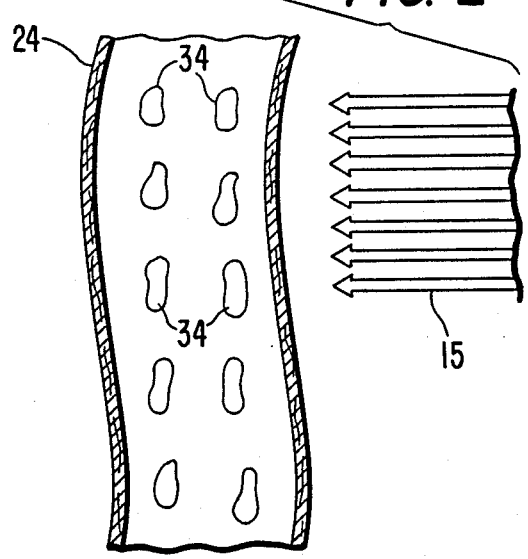
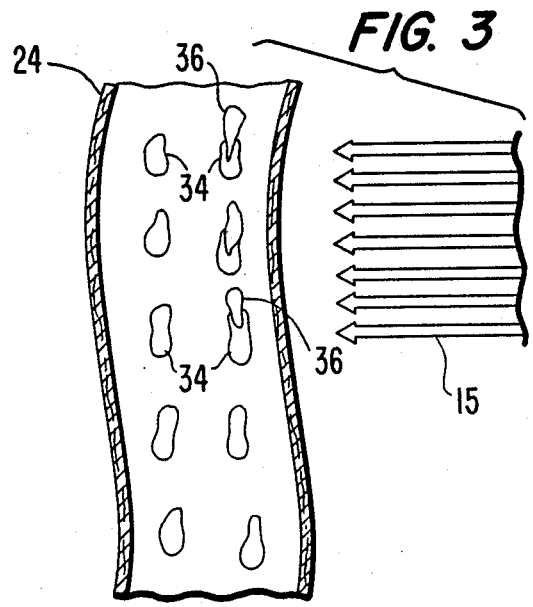

SYSTEM FOR SELECTIVE RELEASE OF LIPOSOME ENCAPSULATED MATERIAL VIA LASER RADIATION

FIELD OF THE INVENTION

The invention relates to a system for the selective release of materials, such as drugs or dyes, at specific sites in the body of an animal. More specifically, the invention relates to a system using a laser to rupture laser light-absorbing and heat-sensitive lipid vesicles which thereby release the drugs or dyes encapsulated therein. The system is advantageously used to selectively deliver drugs or dyes in the eye, although it can also be used with the skin, larynx, uterus, stomach and other organs.

BACKGROUND OF THE INVENTION

The typical manner of administering drugs and dyes to the body is via injection into the bloodstream or a localized area in the body. When injected into the bloodstream, the injected material is carried throughout the blood system and therefore the entire body. This is known as a systemic delivery. The drawbacks to this delivery system are that the concentration of the injected material is extremely diluted and the material acts on most tissues in the body and may be toxic to some of them. In addition, the location and duration of exposure of these injected materials cannot be controlled.

In a localized injection, the location is controlled. Certain organs of the body, such as the eye, cannot be invaded, at least for diagnostic purposes, and local injections are thus not feasible. A sharp, easily visible wavefront of dye or drug, known as a bolus, can be achieved by controlling the injection in the vein. However, a bolus cannot be obtained repeatedly because the material already injected accumulates, causing a background and limiting the dose. Repeated boli can be important where physiological conditions, such as exercise, breathing of oxygen, and sugar level, are altered between them for diagnostic purposes.

In an effort to overcome some of the drawbacks of systemic and local injections of drugs and dyes, lipid vesicles, known as liposomes, have come into use in recent years. The lipid vesicles encapsulate drugs or dyes and can be injected into the bloodstream where they are carried to various organs in which they are naturally ruptured and the encapsulated materials released. The manner of making lipid vesicles is disclosed in, for example, U.S. Pat. No. 4,078,052 to Papahadjopoulos and U.S. Pat. No. 4,241,046 to Papahadjopoulos et al, the disclosures of which are hereby incorporated by reference. While the use of lipid vesicles can improve drug and dye delivery, they also have drawbacks. Thus, traditionally, the concentration of the released encapsulated material and the location and duration of such release cannot be controlled.

In an attempt to obtain some control of the location at which material encapsulated by lipid vesicles is released, microwaves have been applied to heat specific tissue areas after heat-sensitive lipid vesicles have been systemically injected. While these attempts have provided some limited benefits, they likewise have significant drawbacks. First, microwaves have long wavelengths and therefore cannot be narrowly focused to a narrow spot which would be required in treating small vessels and areas of the body. Second, since microwaves cannot be narrowly focused, they tend to heat additional areas of surrounding tissue which may cause damage. Third, microwaves affect the liposomes and the tissue equally by heating up both. Finally, since microwaves have a wavelength in the invisible part of the electromagnetic spectrum, they cannot be observed upon delivery and it is difficult to know whether the microwaves have been properly aimed at the targeted tissue.

Examples of various patents relating to the use of lipid vesicles for delivery of material in the body are disclosed in U.S. Pat. No. 4,310,506 to Baldeschwieler et al; U.S. Pat. No. 4,350,676 to Laties et al; U.S. Pat. No. 4,515,736 to Deamer; U.S. Pat. No. 4,522,803 to Lenk et al; and U.S. Pat. No. 4,610,868 to Fountain et al, the disclosures of which are hereby incorporated by reference.

Examples of the use of heat to release material encapsulate in lipid vesicles, including the use of microwaves, are disclosed in the following publications: Yatvin et al, Design of Liposomes for Enhanced Local Release of Drugs by Hyperthermia, *Science*, Vol. 202, pp. 1290–1292, Dec. 22, 1978; Weinstein et al, Liposomes and Local Hyperthermia: Selective Delivery of Methotrexate to Heated Tumors, *Science*, Vol. 204, pp. 188–191, Apr. 13, 1979; Weinstein et al, Treatment of Solid L1210 Murine Tumors with Local Hyperthermia and Temperature-Sensitive Liposomes Containing Methotrexate, *Cancer Research*, Vol. 40, pp. 1388–1394, May, 1980; and Weinstein et al, Phase Transition Release, A New Approach to the Interaction of Proteins with Lipid Vesicles, Application to Lipoproteins, *Biochimica et Biophysica Acta*, Vol. 647, pp. 270–284, 1981. In addition, U.S. Pat. No. Re. 32,066 to Leveen discloses the use of radio frequency electromagnetic radiation for treating tumors.

SUMMARY OF THE INVENTION

Accordingly, it is a primary object of the invention to provide an improved delivery system in the body of an animal for drugs and dyes that is capable of controlling the concentration, location and duration of the released material.

Another object of the invention is to provide a system for selectively delivering drugs and dyes at a specific site in the body of an animal regardless of whether the material is systemically or locally injected.

Another object of the invention is to provide a system for the selective delivery and release in the body of material encapsulated in laser light-absorbing and heat-sensitive lipid vesicles via use of laser radiation having a wavelength in the visible or infrared part of the electromagnetic spectrum.

Another object of the invention is to provide a system for the selective release of materials inside the body of an animal where the release can be instigated and repeated at desired times.

Another object of the invention is to provide a system for the selective release of materials in the body of an animal where the delivery system uses a laser beam which can be adjusted relative to its location and spot size.

A further object of the invention is to provide a system for the selective release of materials in the body of an animal in which the release can take place in fragile and small tissue areas such as blood vessels in the retina.

A further object of the invention is to provide a system for the selective release of materials at specific sites in the body of an animal including in the eye, skin, larynx, uterus, stomach, and other organs.

The foregoing objects are basically attained by providing a method of selectively releasing a material at a specific site inside the body of an animal, comprising the steps of encapsulating the material in laser light-absorbing and heat-sensitive lipid vesicles, injecting the lipid vesicles into the body, either directly at the specific site or into the bloodstream of the animal so the bloodstream carries the lipid vesicles throughout the body including the specific site, generating a laser beam having a wavelength in the visible or infrared part of the electromagnetic spectrum, and applying the laser beam to the lipid vesicles located at the specific site, thereby heating and rupturing the lipid vesicles so that the material therein is released therefrom at the specific site.

The foregoing objects are also attained by providing an apparatus for selectively releasing a material at a specific site inside the body of an animal by heating and rupturing lipid vesicles containing the material and located at the specific site, the combination comprising a source for generating a laser beam having a wavelength in the visible or infrared part of the electromagnetic spectrum; a first mechanism, located adjacent the source and the specific site, for delivering the laser beam into contact with the specific site; a second mechanism, located adjacent the specific site, for observing the location of the contact between the laser beam and the specific site; and a third mechanism, coupled to the first mechanism, for adjusting the position, size, or both, of the contact relative to the specific site.

Other objects, advantages and salient features of the present invention will become apparent from the following detailed description, which, taken in conjunction with the annexed drawings, discloses a preferred embodiment of the invention.

DRAWINGS

Referring now to the drawings which form a part of this original disclosure:

FIG. 2 is an enlarged diagrammatic view of a blood vessel having lipid vesicles contained therein and being irradiated by a laser beam; and FIG. 3 is an enlarged diagrammatic view similar to that shown in FIG. 2 except that the laser beam has ruptured the lipid vesicles in the blood vessel and a drug or dye encapsulated therein has been released into the blood vessel.

DESCRIPTION OF THE INVENTION

Figure 1:
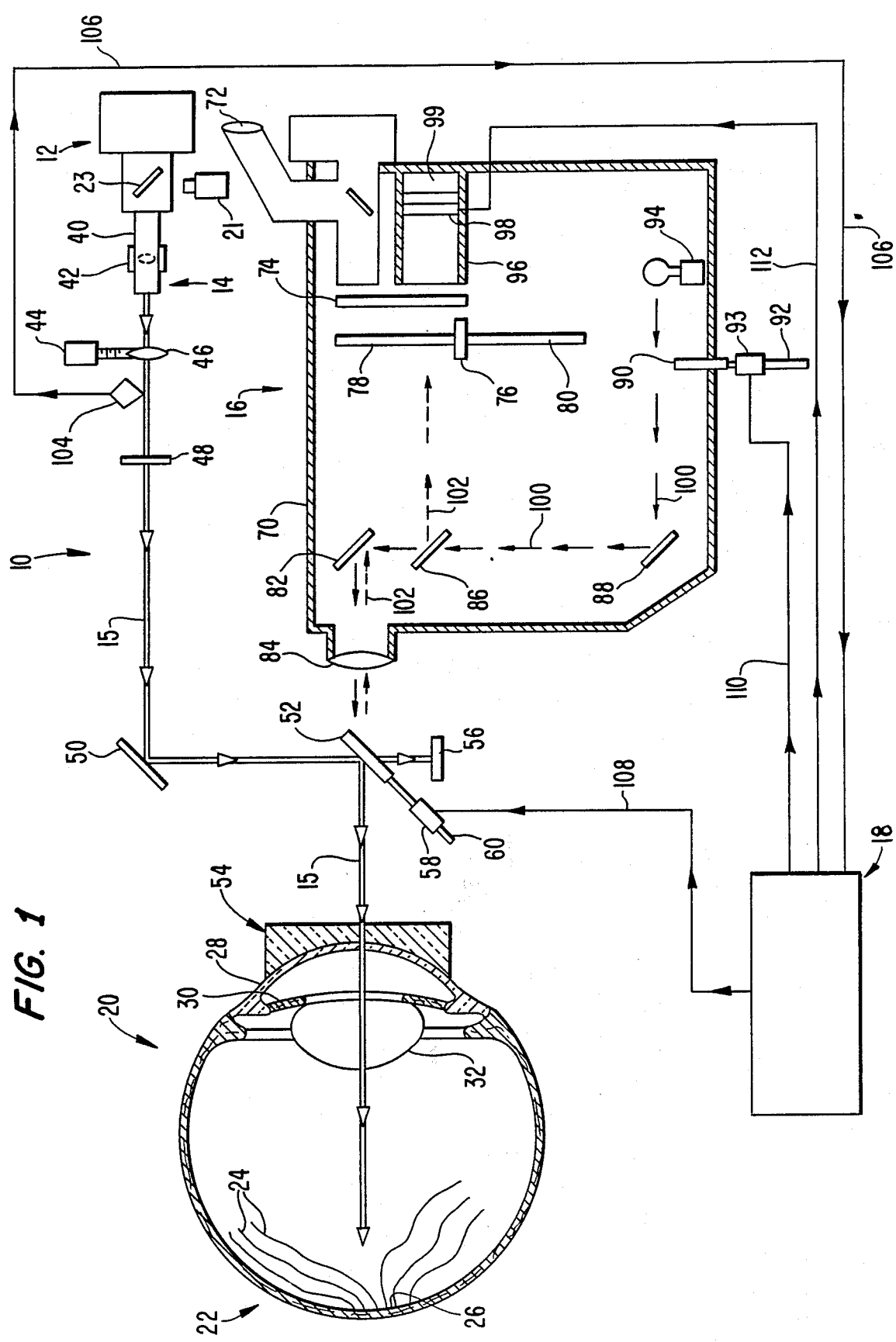
FIG. 1 is a diagrammatic view of the system in accordance with the invention shown in use with an eye and comprising a laser, a system for delivering the laser light to the eye, a system for observing the delivery of the light to the eye, and a control system for coordinating the delivering and observing systems.

Referring now to FIGS. 1-3, the system 10 in accordance with the invention is shown diagrammatically as comprising a laser 12, a delivery system 14 for delivering the laser beam 15 from the laser to a target, an observation system 16 for observing the contact of the laser beam with the target, and a control system 18 for coordinating the delivery and observation systems.

As illustrated in FIG. 1, the overall target is an eye 20 and for purposes of illustration the specific target site 22 to be irradiated by the laser beam is exemplified by blood vessels 24 in the retina 26 in the eye. In addition to the example shown in FIG. 1 regarding blood vessels in a retina, the specific site to be irradiated by the system 10 can comprise the vitreous located inside the eye, the skin, larynx, uterus, stomach or other organs which can be exposed to laser light.

As seen in FIG. 1, the eye 20 further comprises a cornea 28, an iris 30, and a natural lens 32.

Referring to FIGS. 2 and 3, the laser light-absorbing and heat-sensitive lipid vesicles 34, in the form of liposomes, are shown inside a blood vessel 24 in, for example, the retina 26 of the eye 20. The lipid vesicles are made of artificial phospholipids and encapsulate active substances in their inner aqueous phase such as a drug or a dye 36 seen in FIG. 3 being released into the bloodstream upon rupture of the lipid vesicles. The liposomes in accordance with the invention are advantageously prepared from dipalmitoylphosphatidylglycerol (DPPG) and dipalmitoylphosphatidylcholine (DPPC) which exhibit in, for example, blood, dramatic and fast increase in release at the in phase transition temperature of 41° C. Thus, with a rise of only about 4° C. above body temperature, the content of the liposomes is locally released. This, as will be described in more detail hereinafter, is accomplished by irradiating the laser light-absorbing liposomes at the specific site via laser beam 15. The lipid vesicles can be injected into the blood stream or locally adjacent the specific target site.

A suitable dye or tracer material used in accordance with the invention is carboxyfluorescein which is a derivative similar to sodium fluorescein widely used in ophthalmic diagnosis and fluoresces in the green part of the spectrum.

As for suitable drugs used in accordance with the invention, they can include anticoagulants, thrombosis solvents and antibiotics encapsulated in the lipid vesicles.

Upon irradiation by the laser beam 15, the lipid vesicles absorb the light, and thus the energy, from the laser beam, are thereby heated, and then rupture. The walls of the vesicles can be transparent to the laser beam, in which case the material inside, for example a carboxyfluorescein dye, absorbs the light and is heated. Alternatively, the walls of the vesicles themselves can incorporate a light absorbing substance, i.e., a chromophore such as a Nile Red dye. In addition, a light-absorbing liposome can be used such as a fluorescent phospholipid. An example of this is fluorescent DPPE, i.e., N-[5-fluoreceinthiocarbamoyl]-dipalmitoyl-L-$\alpha$-phosphatidylethanolamine [fluorescein-PE].

Turning again to FIG. 1, the laser 12 is advantageously an argon or krypton laser capable of delivering laser beam pulses with each pulse having a duration of about 200 to about 500 milliseconds. The duration between pulses is advantageously between about 100 to about 500 milliseconds. Advantageously, the laser 12 generates a power of 0.1–0.5 watts and the ultimate contact or spot size of the laser beam 15 on the retina 26 is about 0.6 millimeters to about 2.0 millimeters. The energy density at the retina for a 200 millisecond pulse is about 9.7 joules per square centimeter for maximum drug or dye release, although release can occur at a lower and more human eye-permissible dose of 1.8 joules per square centimeter. As will be described in detail hereinafter, the wavelength of the laser beam 15 as it strikes the specific target site is chosen to be in the visible or infrared part of the electromagnetic spectrum, i.e., between about 300 to about 1200 nanometers. Thus, the specific location of the beam spot relative to the specific site, as well as its size, can be observed and adjusted as necessary. Advantageously in use with an eye, the laser beam wavelength is in the blue part of the spectrum and the material encapsulated inside the lipid vesicles readily absorbs light in that wavelength so that the material is heated in order to rupture the lipid vesicles. Since the surrounding tissue tends to absorb the light to a lesser degree, the surrounding tissue does not heat up as much, thus avoiding potential damage.

The delivery system 14 basically comprises a fiber optic cable 40 coupled to the output of the laser 12, a pair of micrometers 42 and 44, a focusing lens 46, a wavelength filter 48, a directional mirror 50, a partial reflector 52, and a contact lens 54 which overlays the cornea 28 on the eye 20.

The fiber optic cable 40 is coupled to the output of the laser 12 to direct the laser beam 15 therefrom. The cable is flexible and can be transversely adjusted in the horizontal direction via actuation of micrometer 42. Located along the light path and adjacent the end of the fiber optic cable is the focusing lens 46 which is coupled to the second micrometer 44 for transverse vertical adjustment. This focusing lens contributes to adjusting the spot size of the laser on the specific site as well as the location thereof by manipulation of micrometer 44. Rather than micrometers, any suitable beam steering mechanism can be used.

The wavelength filter 48 advantageously passes blue light and filters green light and thus has a wavelength setting of about 488 nanometers. If the laser generates blue light, filter 48 can be eliminated. The directional mirror 50 is aligned with the wavelength filter, focusing lens and fiber optic cable and merely redirects the laser beam 15 downward towards the partial reflector 52. This partial reflector advantageously transmits about 50% of the laser light and reflect the other 50%. The 50% transmitted proceeds to any suitable absorber 56, while the reflected 50% is directed at the contact lens 54.

The partial reflector 52 is supported via a plunger 60 that is part of a solenoid 58. The partial reflector is in the position shown in FIG. 1 when the laser is on, but is removed therefrom, i.e., moved to the left and down, when the laser is off and the specific site 22 is being observed and photographed. In essence, the partial reflector 52 is thus moved out of the way of the observation system 16. Rather than a solenoid, any suitable actuating device can be used.

The contact lens 54 on cornea 28 is used to neutralize the normal focusing system of a natural cornea. The contact lens 54 has a flat front surface and allows enlargement of the contact spot of the laser beam 15 on the specific site 22. The contact lens can advantageously be formed of glass or any other suitable material.

If the laser beam 15 has a wavelength in the visible part of the electromagnetic spectrum, it can be observed by the naked eye. If, however, the laser beam has a wavelength in the infrared part of the spectrum, a second helium-neon laser 21 with a visible beam is used in tandem and superimposed with the output of laser 12 to allow observation by the naked eye. In this case, the aiming visible beam from laser 21 is mixed with the output of laser 12 via a one-way reflector 23.

The observation system 16 is in the form of a slit lamp microscope or a fundus camera as seen in FIG. 1, which is suitable for observing and photographing various tissue surfaces. The observation system used in accordance with the invention is a substantially conventional fundus camera except for the addition of two specific elements as will be described in detail hereinafter.

The observation system 16 thus comprises an outer housing 70, a viewing lens 72 for use by an observer, a barrier filter 74 adjacent the viewing lens, a rotating lens holder 76 having a plurality of lenses, such as lenses 78 and 80 thereon, a one-way reflector 82, and a lens 84. Below the first one-way reflector 82 is also a second one-way reflector 86 and below it is a simple reflector 88. Adjacent the reflector 88 is an exciter filter 90 supported on a plunger 92 forming part of a solenoid 93, and adjacent the exciter filter is a flash mechanism 94. The exciter filter 90 is in place when the observation system 16 is taking a photograph but is otherwise moved out of position. Inside the housing 70 is an internal compartment 96 having a shutter 98 and film 99 therein. Rather than using the photographic structure shown in FIG. 1, a single lens reflex structure can be used.

The barrier filter 74 passes fluorescent green light to the viewing lens 72 and film 99 but filters blue light. This type of barrier filter is used in conjunction with carboxyfluorescein, since it fluoresces in th green part of the spectrum. The rotating lens holder 76 is added to the conventional fundus camera to aid in focusing the specific site 22 relative to the observer and the film. While only two lenses 78 and 80 are shown on the rotating lens holder 76, advantageously four different lenses can be used. They preferably have a range of from 1-2.75 diopters in power to compensate for the use of the flat contact lens 54. The lens holder 76 is suitably supported inside the housing and can be manipulated to change its lenses via, for example, a knob on the exterior of the housing.

The one-way reflector 82 is transparent from the right-hand side as shown in FIG. 1 so the observer can view the specific site therethrough. However, on its left-hand side, it reflects light such as that generated by the flash mechanism 94, which is represented via solid arrows 100, and that reflected from the specific site 22, which is represented by dashed arrows 102. The second one-way reflector 86 is transparent on its left-hand side as seen in FIG. 1 so that the light from the flash mechanism can pass upwardly therethrough, but is reflective on its right-hand side so that the returning reflected image of the site 22 is reflected through the shutter 98 and onto the film 99.

The exciter filter 90 transmits blue light from the flash mechanism in the example set forth herein since the material encapsulated in the lipid vesicles becomes visible in blue light. In addition to the use of lenses in the rotating lens holder discussed above, the control of the exciter filter 90 and the associated solenoid are added to the conventional fundus camera.

The control system 18 is basically a timing system with conventional elements for the selective actuation of the solenoids 58 and 93 as well as the shutter 98.

The control system 18 receives an input signal via a photodetector 104, located between micrometer 44 and wavelength filter 48, and input line 106. Extending from the control system is an output line 108 coupled to solenoid 58 and output line 110 coupled to the second solenoid 93. Finally, there is an output line 112 extending from the control system to the shutter 98.

Thus, when the laser pulse is actuated, as seen in FIG. 1, reflector 52 is in place but exciter filter 90 is out of the line of light from the flash mechanism 94. When the laser pulse ends as detected by the photodetector 104, the partial reflector 52 is withdrawn and the exciter filter 90 is moved into place. At that time, a picture can be taken. Preferably, the illumination from the flash mechanism remains on during the entire operation of the system.

By adjusting the micrometers 42 and 44, the location and spot size of the laser beam on the specific site 22 can be readily adjusted. Likewise, the location of the spot size can be varied via the contact lens 54.

Since the output of laser 12 and laser 21 are visible, an observer can use the observation system 16 to locate the contact spot of the laser beam relative to the specific target site and adjust the location as well as the size of the spot. In addition, since the laser beam can be focused, it can be targeted at extremely small blood vessels such as those located in the eye.

As seen diagrammatically in FIG. 2, the lipid vesicles 34 are shown in their unruptured state in the blood vessel 24 with the laser beam 15 about to act on them. In the case of carboxyfluorescein, the dye does not fluoresce at this point since the concentration in the vesicles is high enough to cause quenching. In FIG. 3, the laser beam 15 has irradiated the lipid vesicles 34 and ruptured them due to light absorption and heating. Upon rupture of the vesicles, the encapsulated material 36 is released therefrom and flows into the bloodstream where the dye is diluted in the blood plasma and fluoresces strongly. The release can either provide a discernible view of flow patterns inside the vessel and/or provide a drug to the specific target site in the blood vessel. In addition, this release allows for measurement of blood flow through blood vessels and organs.

By using the system 10 in accordance with the invention, a localized irradiation of the lipid vesicles is produced whose location, duration and instigation can be controlled. In addition, heating of surrounding tissue is minimized since the laser beam is mainly absorbed by the chromophores in the lipid vesicles. Moreover, delivery of dyes and drugs can be repeated as often as necessary or desired as long as the lipid vesicles are present at the irradiated site.

While one advantageous embodiment has been chosen to illustrate the invention, it will be understood by those skilled in the art that various changes and modifications can be made therein without departing from the scope of the invention as defined in the appended claims. For example, as illustrated in FIG. 1, the laser beam acts directly on the retina as it passes through the transparent anterior portions of the eye. However, the system in accordance with the invention can also be used on tissue or vessels in the body not directly accessible via a laser beam through the use, for example, of an elongated fiber optic cable or other delivery system.

What is claimed is:

1. A method of selectively and repetitively releasing a material at a specific site in the blood stream inside the body of an animal, comprising the steps of
   encapsulating the material in heat-sensitive lipid vesicles,
   injecting the lipid vesicles into the blood stream of the animal so that the blood stream carries the lipid vesicles throughout the body including the specific site,
   generating a laser beam having a wavelength in the visible or infrared part of the electromagnetic spectrum, and
   applying the laser beam to the lipid vesicles located at the specific site so as to heat and rupture the lipid vesicles so that the material therein is released within milliseconds therefrom at the specific site.

2. A method according to claim 1, wherein the material in the lipid vesicles comprises a dye.

3. A method according to claim 1, wherein the material in the lipid vesicles comprises a drug.

4. A method according to claim 1, wherein the specific site is in the retina.

5. A method according to claim 1, wherein the specific site is in the eye.

6. A method according to claim 1, wherein
   the wavelength of the laser beam is in the blue part of the spectrum.

7. A method according to claim 1, and further comprising the step of
   photographing the specific site.

8. A method according to claim 1, wherein
   the specific site is in the retina in an eye, and
   the applying step is preceded by the step of placing a contact lens on the cornea of the eye to enlarge the spot size of the laser beam inside the eye.

9. A method according to claim 1, wherein
   the material absorbs light at a wavelength corresponding to the wavelength of the laser beam.

10. A method according to claim 1, wherein the applying step comprises the steps of
    aiming the laser beam at the specific site,
    observing the location of the contract between the laser beam and the specific site, and
    adjusting the position of the contact relative to the specific site.

11. A method according to claim 1, and further comprising the steps of
    observing the size of the contact between the laser beam and the specific site, and
    adjusting the size of the contact.

* * * * *